United States Patent
Dextradeur et al.

(10) Patent No.: US 9,636,017 B2
(45) Date of Patent: May 2, 2017

(54) TELEMETRIC DOCKING STATION

(71) Applicant: DePuy Synthes Products, INC., Raynham, MA (US)

(72) Inventors: Alan Dextradeur, Franklin, MA (US); Douglas Fifolt, Wrentham, MA (US); Eugene Szczecina, Monmouth Junction, NJ (US); Kenneth Creasy, Lakeville, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1031 days.

(21) Appl. No.: 13/798,439

(22) Filed: Mar. 13, 2013

(65) Prior Publication Data

US 2014/0276180 A1    Sep. 18, 2014

(51) Int. Cl.
*A61B 5/00* (2006.01)
*A61B 5/03* (2006.01)
(Continued)

(52) U.S. Cl.
CPC .......... *A61B 5/0006* (2013.01); *A61B 5/0031* (2013.01); *A61B 5/031* (2013.01); *A61B 5/6864* (2013.01); *A61B 5/6868* (2013.01); *A61B 5/0478* (2013.01); *A61B 5/6882* (2013.01); *A61B 2560/0214* (2013.01);
(Continued)

(58) Field of Classification Search
CPC ..... A61B 5/031; A61B 5/0031; A61B 5/6864; A61B 5/6868; A61B 5/6882; A61B 2560/0214; A61B 2560/0443; A61B 2560/045; A61B 2562/0247; A61B 2562/0261; A61B 2562/225;
(Continued)

(56) References Cited

U.S. PATENT DOCUMENTS

| 4,246,908 A | 1/1981 | Inagaki et al. |
| 5,971,931 A | 10/1999 | Raff |

(Continued)

FOREIGN PATENT DOCUMENTS

| EP | 2449966 A1 | 5/2012 |
| TW | M 374 842 U | 3/2010 |
| WO | 2012011780 A2 | 1/2012 |

OTHER PUBLICATIONS

European Search Report mailed on Sep. 4, 2015, issued in corresponding Application No. 15168708.4-1657.
(Continued)

*Primary Examiner* — Devin Henson
(74) *Attorney, Agent, or Firm* — Troutman Sanders LLP

(57) ABSTRACT

A modular sensor system is disclosed. The system can include one or more sensors, a mounting unit, and a control unit. The mounting unit can enable the control unit and/or one or more sensors to be securely, but detachably, mounted to a patient's body. The control unit can include electronics and other components configured to interface with, monitor, and record data from the one or more sensors. The control unit can further include a wired bus, transceiver, antenna, or other suitable components to enable wireless communication between the system and a central control or monitor. Some or all of the components included in the control unit can be removable from the system to enable some or all of the electronics of the system to be removed.

5 Claims, 6 Drawing Sheets

(51) Int. Cl.
   *G01L 19/14* (2006.01)
   *A61B 5/0478* (2006.01)

(52) U.S. Cl.
   CPC . *A61B 2560/045* (2013.01); *A61B 2560/0406* (2013.01); *A61B 2560/0443* (2013.01); *A61B 2562/00* (2013.01); *A61B 2562/0247* (2013.01); *A61B 2562/0261* (2013.01); *A61B 2562/16* (2013.01); *A61B 2562/225* (2013.01); *A61B 2562/227* (2013.01); *G01L 19/142* (2013.01); *G01L 19/143* (2013.01); *G01L 19/144* (2013.01)

(58) Field of Classification Search
   CPC .......... A61B 2562/227; A61B 2562/16; G01L 19/142; G01L 19/143; G01L 19/144
   See application file for complete search history.

(56) References Cited

U.S. PATENT DOCUMENTS

| | | | |
|---|---|---|---|
| 6,083,174 A | 7/2000 | Brehmeier-Flick et al. | |
| 6,248,080 B1 | 6/2001 | Miesel et al. | |
| 6,315,719 B1 | 11/2001 | Rode et al. | |
| 6,560,486 B1 | 5/2003 | Osorio et al. | |
| 6,603,995 B1 | 8/2003 | Carter | |
| 7,301,452 B2 | 11/2007 | Gerder et al. | |
| 7,844,315 B2 | 11/2010 | Al-Ali | |
| 8,174,395 B2 | 5/2012 | Samuelsson et al. | |
| 2006/0282001 A1 | 12/2006 | Noel et al. | |
| 2008/0161659 A1 | 7/2008 | Reichenberger et al. | |
| 2008/0242962 A1 | 10/2008 | Roesicke et al. | |
| 2008/0287752 A1 | 11/2008 | Stroetz et al. | |
| 2009/0005701 A1 | 1/2009 | Dextradeur et al. | |
| 2009/0124880 A1 | 5/2009 | Smith | |
| 2009/0292179 A1 | 11/2009 | Jampala et al. | |
| 2010/0030103 A1 | 2/2010 | Lutze et al. | |
| 2010/0217108 A1 | 8/2010 | Tauber et al. | |
| 2011/0009716 A1 | 1/2011 | Gohler et al. | |
| 2011/0028822 A1* | 2/2011 | Beck | A61B 5/0408 600/386 |
| 2011/0071370 A1 | 3/2011 | Al-Ali | |
| 2011/0160609 A1* | 6/2011 | Stone | A61B 3/16 600/561 |
| 2012/0059231 A1* | 3/2012 | Frey | A61B 5/14532 600/309 |
| 2012/0245438 A1* | 9/2012 | Bernini | A61B 5/0031 600/309 |
| 2012/0296187 A1 | 11/2012 | Henning | |
| 2012/0296444 A1 | 11/2012 | Greenberg | |

OTHER PUBLICATIONS

Partial European Search Report for EP 14 15 9024 dated Jun. 26, 2014—Foreign Counterpart to the present application.
European Search Report for EP 14 15 9024 dated Oct. 28, 2014—Foreign Counterpart to the present application.

* cited by examiner

TELEMETRIC DOCKING STATION

FIELD OF THE INVENTION

The present invention relates generally to telemetric sensors, and more specifically to modular telemetric sensors with detachable electronics for the monitoring of one or more brain functions.

BACKGROUND

A variety of internal and external sensors exist to monitor brain parameters. Electroencephalography (EEG), for example, utilizes a plurality of external electrical sensors, attached to the scalp, to monitor electrical activity in the brain. The EEG can be used clinically to detect anomalies (such as epilepsy), diagnose sleep issues, and determine the severity of brain injury after an accident, among other things. In the event of serious brain injury, for example, the EEG can be used to differentiate between coma, vegetative state, and complete brain death.

In the event of brain injury and/or infection, for example, the brain has a tendency to swell. As the brain swells, it compresses the surrounding intracranial fluid, increasing the pressure on the brain. Unfortunately, this pressure can damage the brain physically and can reduce blood flow to the brain causing oxygen deprivation and possible death to brain tissue. This secondary type of brain injury is often more extensive than the original injury to the brain (e.g., from a head trauma).

After injury or infection, therefore, it can be beneficial to monitor intracranial pressure (ICP) for several hours or days to ensure the brain edema subsides and to prevent further injury. This overpressure situation can often be reduced, or eliminated, for example, simply by draining a portion of the cerebral fluid out of the skull through a burr hole. In less severe cases, brain swelling and brain tissue oxygen demand can be reduced by externally cooling the brain. This can enable the swelling to subside naturally, which may obviate the need for a burr hole.

In either case, an intracranial pressure sensor inserted directly into the skull can provide accurate ICP readings. These sensors can be simple capillary type sensors connected to an external gauge, for example, or can be electronic gauges based on strain gauge, or other technologies. A problem with conventional mechanical and electronic gauges, however, is that they generally require an external connection to be read. A capillary type gauge, for example, must be connected to a dial, or other apparatus, to read the ICP. Electronic gauges, on the other hand, can require wires, or other means, to be attached to the patient to enable monitoring. The attached wires can increase patient discomfort by pulling on the wound site and increasing infection and can also cause accidents resulting from entanglement of the wires, among other things.

In addition, many patients that receive invasive ICP monitoring have limited consciousness and, as a result, may have limited, or no, mobility. As a result, they generally must be, for example, handled, turned, and moved by caregivers to facilitate bathing and sheet changes, among other things. During handling, the cables and wires from conventional sensors can be accidentally pulled or broken by the caregivers. This, in turn, can result in sensors breaking or pulling out of the brain tissue and a loss of functionality. When this happens, a new sensor must be placed in a new location resulting in an additional procedure, additional disruption of brain tissue, and additional cost to the hospital.

To address these issues, wireless sensors have been developed. Unfortunately, these too suffer from a number of drawbacks. One type of wireless sensor, for example, as disclosed in U.S. Patent Pub. No. 2010/0030103, includes a sensor, an external coil, or antenna, for communication. This type of sensor possesses no internal memory or other storage. To collect data from the sensor, therefore, an interrogator must be placed in close proximity to the sensor at all times. This "semi-wired" configuration, in which the sensor must be read externally with a reader, substantially defeats the purpose of the wireless component of the sensor.

In addition, conventional sensors have electronic components that are permanently, or semi-permanently, implanted in, or attached to, the patient's body. In this configuration, the many components of the sensor, which can include, for example, antennas, batteries, silicon chips, RFID chips, and other electronic components, generally cannot be removed without removing the entire sensor. Depending on the application, this may require involved procedures, even including surgical intervention. These components can, at a minimum, interfere with ongoing testing such as X-rays, MRIs, and other imaging. At worst, these components can actually injure the patient. Batteries and other metallic objects, for example, can actually physically move or be heated to the point of explosion by magnetic resonance imaging (MRI). In addition, many components may be rendered inoperable by x-rays and other radiation.

What is needed, therefore, is a wireless, modular sensor capable of reading one or more bodily functions. The sensor should be modular, such that some, or all, of its components can be easily removed for testing and then reinstalled. The sensor should include a secure mounting solution to enable removal and installation of these components with little or no discomfort to the patient. It is to such a system that examples of the present invention are primarily directed.

SUMMARY

Examples of the present invention relates generally to telemetric sensors, and more specifically to modular telemetric sensors with removable electronics for the monitoring of one or more brain functions. In some examples, the system can generally include a sensor, a mounting unit, and a control unit. The mounting unit can provide a secure mounting location for the sensor and/or control unit on the patient's body. For the monitoring of ICP and other intracranial functions, for example, the mounting unit can have a collar press-fit into a burr hole in the patient's skull.

In some examples, the control unit can have electronics and/or batteries for monitoring, storing, and analyzing data from the sensor. In some examples, the control unit can have a detachable battery to provide power to the system, yet enable battery removal when necessary. This can be useful, for example, when an MRI is performed, to prevent overheating of the battery.

In some examples, the control unit can include an upper control unit and a lower control unit. In this configuration, "safe" electronics can be housed in the lower control unit, while "unsafe" electronics can be housed in the upper control unit. Both the upper and lower control units can be detachably coupled to the mounting unit, or to an electronics interface that is, in turn, mounted to the control unit. The segregation of safe and unsafe electronics can enable electronics or batteries that present issues for a particular procedure to be easily and/or temporarily removed from the system.

Examples of the present invention can include a sensor system comprising a sensor monitoring one or more bodily functions of a patient's body, a control unit comprising one or more electronic components in communication with the sensor, and a mounting unit detachably coupling the control unit and the sensor to the patient's body. In some examples, removing the control unit from the mounting unit removes a portion of the one or more electronic components from the patient's body. In some examples, the one or more electronic components can include a battery. In other examples, the control unit can include a battery and one or more additional electronic components. Conveniently, the battery can be detachably coupled from the control unit without removing the one or more additional electronic components.

In some examples, the mounting unit can have a collar that can be press-fit into a burr hole in the patient's skull. In other examples, the mounting unit can include an electronics interface detachably coupling the control unit to the mounting unit. In still other examples, removing the control unit removes all electronic components from the sensor system.

Examples of the present invention can also include a sensor system with a sensor disposed inside of and monitoring one or more bodily functions of a patient's body and a control unit in communication with the sensor. In some configurations, the control unit can have electronics, including but not limited to, a processor receiving and processing signals from the sensor, a memory storing data transmitted over the signals, and an interface receiving and transmitting data. The system can also include a mounting unit detachably coupling the control unit to the patient's body.

In some examples, the interface can be a wireless transceiver wirelessly transmitting and receiving data at the control unit. In some examples, the interface can further include, for example, an antenna or a wired bus transmitting and receiving data at the control unit. In some examples, the control unit can be powered by a battery. For ICP applications, for example, the system can include a strain-type pressure gauge measuring intracranial pressure (ICP).

Examples of the present invention can also include a sensor system with a sensor for monitoring one or more bodily functions of a patient's body, a lower control unit comprising a first group of one or more electronic components in communication with the sensor, an upper control unit comprising a second group of one or more electronic components in communication with the sensor and a mounting unit detachably coupling the upper and lower control unit to the patient's body. In some examples, removing the upper control unit and the lower control unit from the mounting unit removes all electronic components from the patient's body.

In other examples, the first group of one or more electronic components can be classified as "safe" electronics and the second group of one or more electronic components can be classified as "unsafe" electronic components. If the system is used in conjunction with an MRI, for example, the first, safe group of one or more electronic components can be non-ferrous containing electronic components and the second, unsafe group of one or more electronic components can be ferrous containing electronic components. If the system is used in conjunction with optical imaging, on the other hand, the first group of one or more electronic components can be optically transparent and the second group of one or more electronic components can be optically opaque.

In some examples, the system can include an electronics interface detachably coupled to the mounting unit and the upper and lower control units can be detachably coupled to the electronics interface. In some examples the electronics interface can be integral to the mounting unit (i.e., they can be manufactured from a single piece of material. In some examples, the battery can be housed in, or integral to, the upper control unit. The battery can be detachably coupled to the upper control unit, for example, such that the battery is removable from the sensor system without removing the upper control unit.

BRIEF DESCRIPTION OF THE DRAWINGS

These and other objects, features and advantages of the present invention will become more apparent upon reading the following specification in conjunction with the accompanying drawing figures.

DETAILED DESCRIPTION

Figure 1:
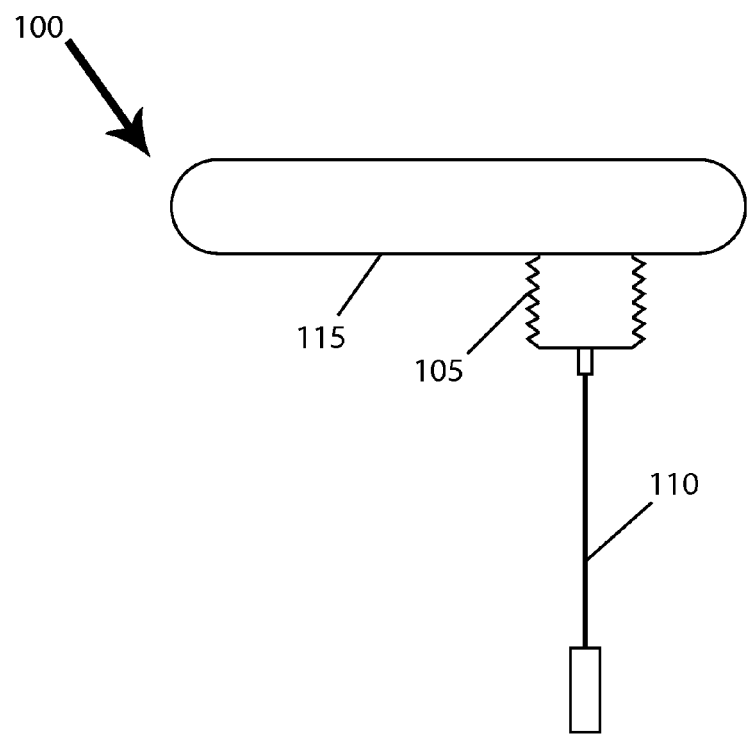
FIG. 1 depicts a modular intracranial pressure (ICP) sensor with removable electronics, in accordance with some examples of the present invention.

The present invention relates generally to telemetric sensors, and more specifically to modular telemetric sensors with detachable electronics for the monitoring of one or more brain functions. In some examples, the sensor can include a mounting unit, one or more sensors, and a control unit. In some examples, the control unit can have some or all of the electronics necessary to operate, read, and/or store data from the one or more sensors. In some examples, the control unit can further include a battery, or battery pack, for powering the sensors and/or electronics during use. In other examples, the control unit can have one or more wireless components to enable wireless, remote operation. In still other examples, the control unit can includes one or more RFID components to enable wireless, remotely powered operation.

To simplify and clarify explanation, the system is described below as a system for monitoring intracranial pressure (ICP) using a strain gauge type pressure sensor. One skilled in the art will recognize, however, that the invention is not so limited. The system can also be deployed to monitor a number of additional bodily functions simply by appropriately locating the one or more sensors and choosing the appropriate sensor package. The system can be deployed to monitor, for example and not limitation, blood pressure, blood flow, body, skin, or organ temperatures, or brain activity simply by employing the appropriate sensor (s).

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

As discussed above, a problem with conventional sensors for monitoring body vitals, and particularly ICP, has been that they generally utilize a wired, or "semi-wired" design. As a result, the patient must be tethered (literally or practically) to monitoring devices to retrieve data from the sensor. In the wired case, these wires can result in accidents (i.e., trip and falls) and/or property damage due to entanglement of the attendant wiring. In addition, the wires pulling on the wound site can be an irritant to the patient and can cause infection and other complications, among other problems. Sensor damage due to patient manipulation and interference with testing (e.g., MRIs) are also major concerns. This risk is only slightly mitigated in the semi-wired case discussed above, as this type of sensor is useless without an external reader, which must be placed in close proximity to the sensor to obtain data and does not provide for ready removal of certain electronics.

In response, as shown in FIG. 1, examples of the present invention can include a wireless sensor system 100. In some examples, the sensor system 100 can have a mounting unit 105, one or more sensors 110, and a control unit 115. In some examples, the control unit 115 can be detachably coupleable to the mounting unit 105 and/or sensors 110 to enable testing or other procedures to be carried out. The control unit 115 can provide a number of features including, but not limited to, battery power, wired and wireless communications, data storage, processing, and data analysis.

For the monitoring of ICP, the sensor 110 can include, for example and not limitation, a strain gauge or capacitive based pressure sensor. For the monitoring of other bodily functions, the sensor 110 can incorporate many types of sensors for monitoring, for example and not limitation, blood pressure, blood flow, blood oxygen levels, EKG, EEG, and internal or external temperatures.

Figure 2:
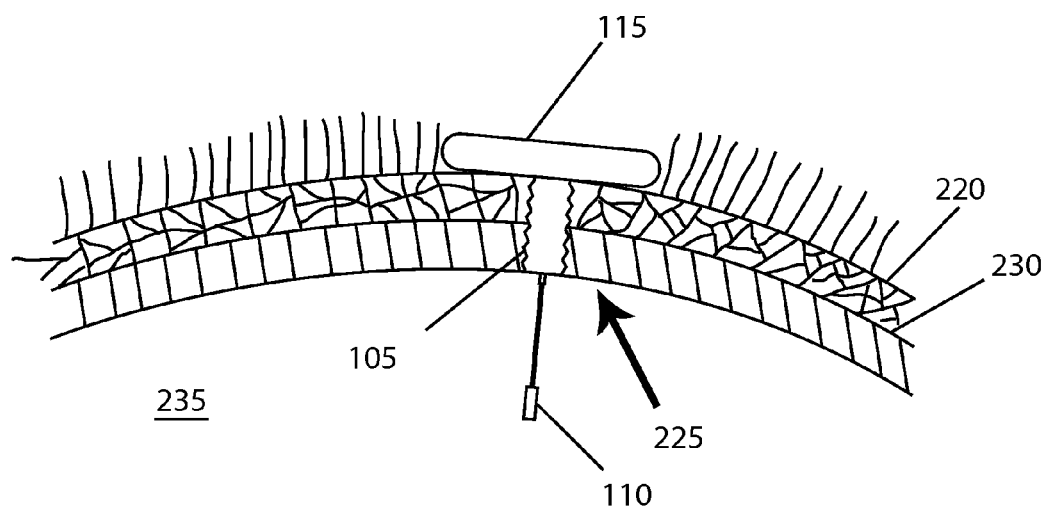
FIG. 2 depicts the sensor of FIG. 1 inserted into a burr hole in a patient's skull, in accordance with some examples of the present invention.

In some examples, as shown in FIG. 2, the mounting unit 105 can have a device suitable to securely and comfortably mount the one or more sensors 110 and the control unit 115 to the patient's body. As shown, when used for monitoring ICP, for example, an incision can be made in the patient's scalp 220 and a burr hole 225 can be bored through the skull 230 for access to the intracranial cavity (ICC) 235.

The sensor 110 can be inserted into the ICC to an appropriate depth, generally 2-3 cm, and can be affixed to the mounting unit 105 or the control unit 115, as desired. In some examples the sensor 110 can be affixed to the mounting unit 105 to enable the control unit 115 to be removed without disturbing the sensor 110. This may be useful, for example, when removing the sensor 110 has a significant risk of injury, discomfort, or infection to the patient and/or when the sensor 110 has little or no effect on additional procedures (e.g., the sensor is non-magnetic in the case of an MRI). In other examples, the sensor can be attached to the control unit 115 to enable the control unit 115 and sensor 110 to be removed as a unit. This may be useful, for example, when the sensor 110, or sensor material, interferes with a particular procedure.

As shown, the mounting unit 105 can frictionally engage the burr hole 225 to securely mount the system 100 to the patient's skull 230. In some examples, the mounting unit 105 can also provide a fluid-tight seal to prevent the loss of bodily fluids [e.g., intracranial fluid (ICF), blood, etc.] and to prevent the introduction of dirt, bacteria, viruses, and other pathogens into the wound site. In some examples, the mounting unit 105 can further accommodate the use of antiseptic and/or antibacterial agents such as, for example and not limitation, Bactiseal® to further prevent infection.[1] In other examples, the mounting unit 105 can be coated with antiseptic or antibacterial substances, or can have these substances integrated directly into the material.

[1]Bactiseal is an antimicrobial polymer for use in infection prevention in and around wound sites owned by the Depuy Companies. See, e.g., U.S. Pat. No. 4,917,686.

Figure 3:
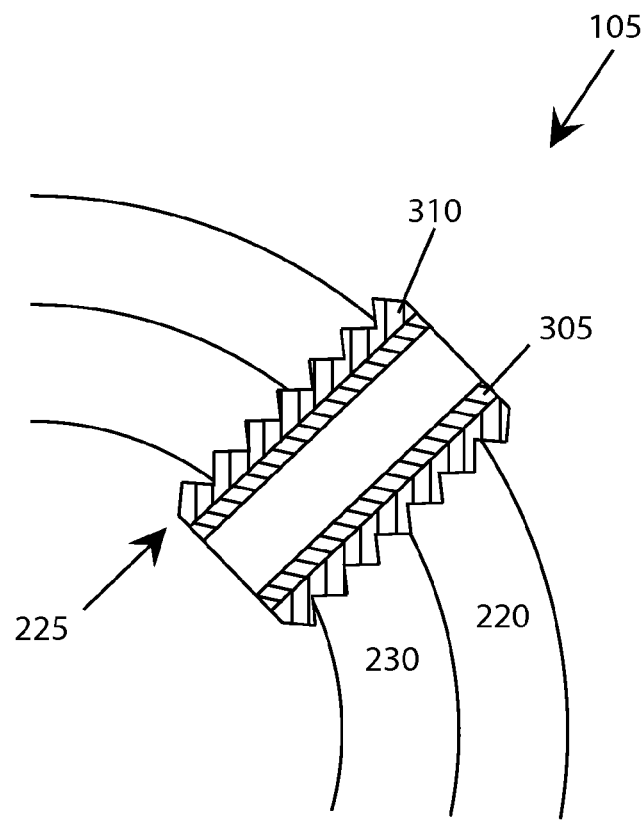
FIG. 3 depicts a detailed view of a mounting unit inserted into a burr hole in a patient's skull, in accordance with some examples of the present invention.

As shown in FIG. 3, in some examples, the mounting unit 105 can include a rigid, or semi-rigid, core 305 with a plurality of externally mounted flexible ribs 310. The ribs 310 can enable the mounting unit 105 to form a fluid-tight seal between, and can increase the frictional engagement of, the mounting unit 105 with the skull 230. In this manner, the mounting unit 105 can provide sufficient carrying capacity to mount the control unit 115 and sensor(s) 110 in a secure and comfortable manner for the patient. In other examples, for internal or external mounting locations, the mounting unit 105 can utilize, for example and not limited to, straps, expanding inserts, mechanical threads, or adhesives for retention, depending upon the applications.

Figure 4:
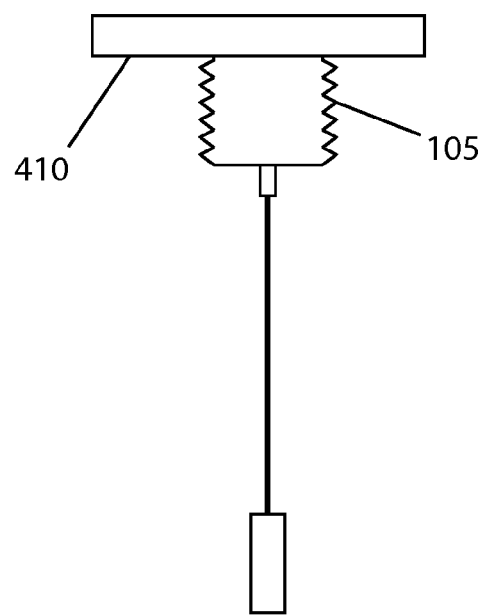
FIG. 4 depicts the mounting unit of FIG. 3 with an electronics interface, in accordance with some examples of the present invention.

As shown in FIG. 4, in some examples, the mounting unit 105 can further have an electronics interface 410 to enable the control unit 115 and one or more sensors 110 to be detachably coupled to the mounting unit 105. The electronics interface 410 can provide a stable platform to attach the control unit 115 and can be detachably coupled to the mounting unit 105. In some examples, the mounting unit 105 and the electronics interface 410 can be integral components. In other words, in some examples, the mounting unit 105 and electronics interface 410 can be integrally cast, molded, or otherwise manufactured, from a single piece of material.

In some examples, the electronics interface 410 can be detachably coupled to the mounting unit 105 and the control unit 115 can be detachably or permanently coupled to the electronics interface 410. These components 105, 410, 115 can be detachably coupled using, for example and not limitation, snaps, clips, straps, magnets, or a combination thereof. The components 105, 410, 115 can be coupled such that they are securely mounted, yet can be removed when desired without injuring the patient or dislodging the mounting unit, for example.

Figure 5:
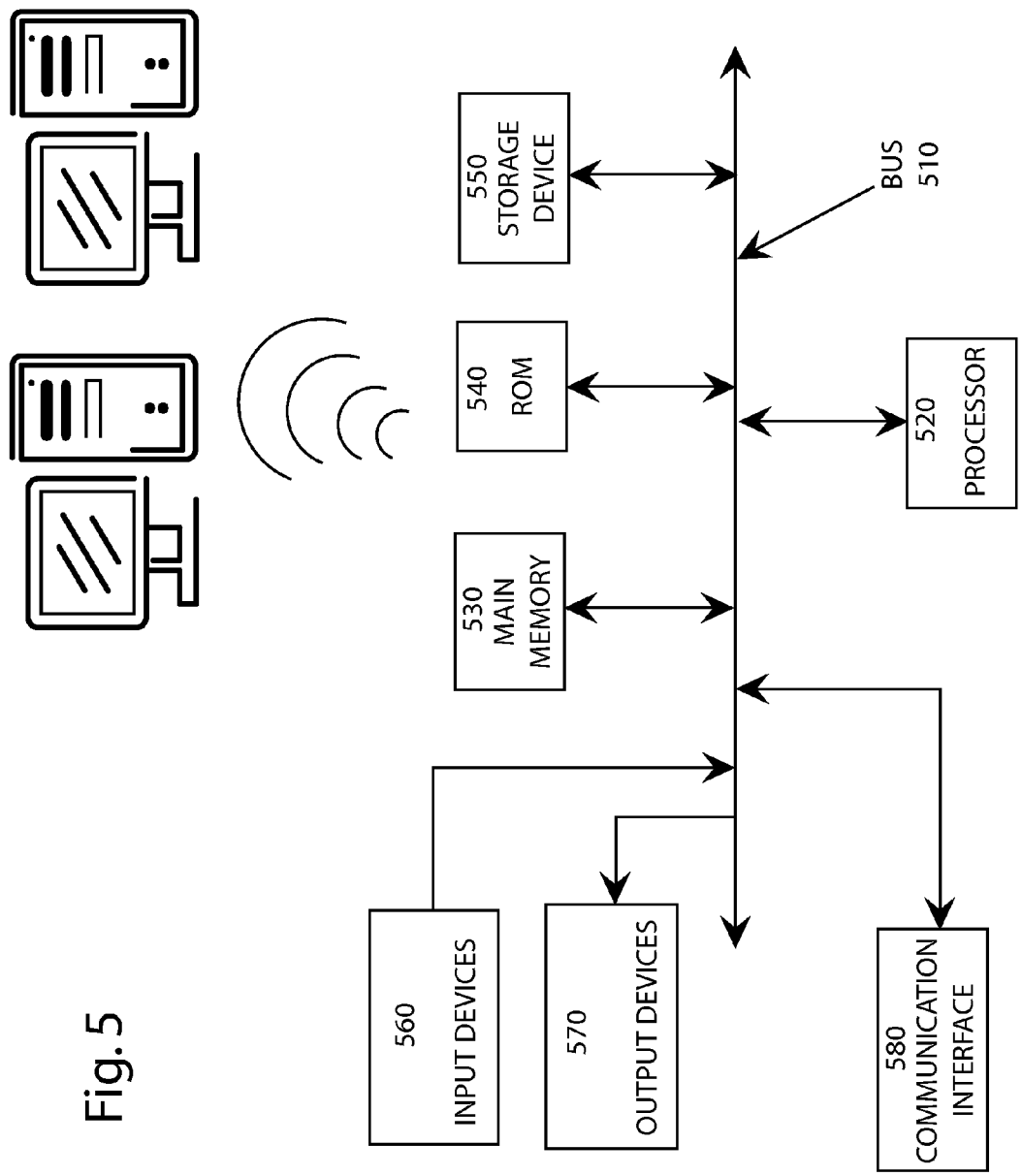
FIG. 5 depicts an electronics package for the modular sensor, in accordance with some examples of the present invention.

As shown in FIG. 5, in some examples, the control unit 115 can have a plurality of electronic components to enable the control unit 115 to, for example, communicate with the one or more sensors 110, analyze and store data therefrom, and transmit and receive data to/from a central control 590 or other monitor. A person of ordinary skill in the art will recognize that these functions can be performed with a variety of components in a variety of configurations.

Various implementations of the control unit 115 can be embodied in transitory or non-transitory computer readable media for execution by a computer processor. FIG. 5 is a diagram of an example architecture of the control unit 115, in an implementation consistent with the disclosed technology. As shown, the control unit 115 can include a bus 510, a processor 520, a main memory 530, a read only memory (ROM) 540, a storage device 550, one or more input devices 560, one or more output devices 570, and a communication interface 580. The bus 510 may include one or more conductors that permit communication among the components of the control unit 115.

The processor 520 can be one or more conventional processors or microprocessors that interpret and execute instructions, such as instructions for providing aspects of the disclosed technology. The main memory 530 may include a random access memory (RAM) or another dynamic storage device that stores information and instructions for execution by the processor 520. The ROM 540 may include a conventional ROM device or another type of static storage device that stores static information or instructions for use by the processor 520. The storage device 550 may include non-volatile memory including, but not limited to, flash memory or SD cards.

The input devices 560 may include one or more mechanisms that permit an operator to input information or programming to the control unit 115, such as a USB, or other cabled connection, keyboard, a mouse, a pen, or voice recognition. The output devices 570 may include one or more mechanisms that output information to an operator or to the central control 590, including a display, a printer, or a speaker. The communication interface 580 may include any transceiver-like mechanism that enables the control unit 115 to communicate with remote devices or systems, such as a mobile device, computing device, or the central control 590 to which data is delivered. The communication interface 580 may include mechanisms for communicating over a network, for example, and can be connected directly or wirelessly to the central control 590 or other components.

As discussed above, the control unit 115 can store and/or process data provided by the sensor(s) 110, manage data, create messages, or other reports, to deliver the data to the central control 590 or other recipient (e.g., a text message to a doctor or nurse containing sensor data or a summary thereof). The control unit 115 may perform tasks to that end in response to the processor 520 executing software instructions contained in a computer-readable medium, such as the memory 530. The software instructions may be read into memory 530 from another computer-readable medium, such as the data storage device 550, or from another device via the communication interface 580. Alternatively, or additionally, hardwired circuitry may be used in place of or in combination with software instructions to implement processes consistent with the disclosed technology. Thus, the disclosed technology is not limited to any specific combination of hardware circuitry and software.

As shown in FIGS. 6a-6d, in some examples, the control unit 115 can further have one or more batteries 620. In some examples, the battery 620 can be integral to the control unit 115. In this configuration, the battery can be charged using an external power cord, for example, or can be charged by removing the control unit 115 and placing it on an inductive charger. In other examples, the battery 620 can be detachably coupled to the control unit 115 to enable the battery to be removed and placed in a separate charger.

Figure 6A:
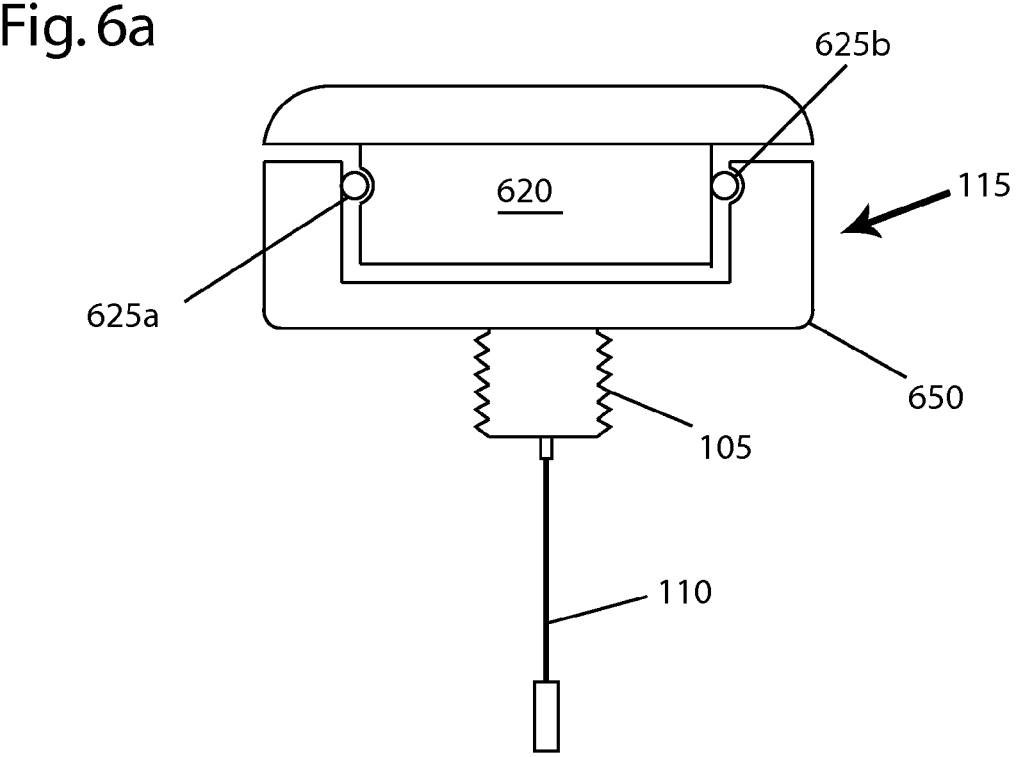
FIG. 6a depicts a modular sensor with a detachable battery pack, in accordance with some examples of the present invention.

The control unit 115 and/or battery 620 can be detachably coupled to the system 100 in number of convenient ways. As shown in FIG. 6a, the control unit 115 can have a cradle 650 for the battery 620 such that the battery 620 snaps, or is otherwise retained, in the control unit 115. The control unit 115 and battery 620 can include one or more complementary contacts 625a, 625b to provide electrical connection therebetween.

Figure 6B:
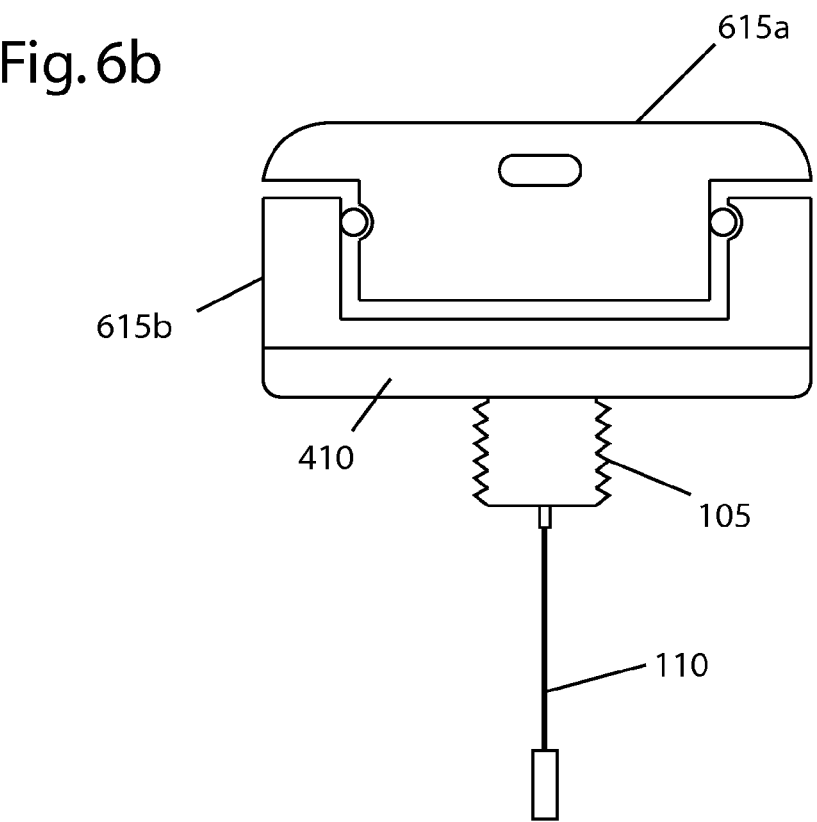
FIG. 6b depicts a modular sensor with an upper and lower control unit, in accordance with some examples of the present invention.

In other examples, shown in FIG. 6b, the control unit can have an upper control unit 615a and a lower control unit 615b. In some examples, for example, the battery 620 and a portion of the electronics can be housed in the upper control unit 615a, while the remainder of the electronics can be housed in the lower control unit 615b. In some examples, the control unit 615 can be mounted on the aforementioned electronics interface 410. In this manner, battery 620 and the control unit 115 can be removed as a unit, leaving the relatively inert electronics interface 410 and mounting unit 105 on the patient.

In still other examples, the upper control unit 615a can house a first set of electronics integrally with the battery 620 and second set of electronics integrally with the lower control unit 615b. In this manner, relatively "safe" electronics can be packaged in the lower control unit 615b, while "unsafe" electronics can be housed in the upper control unit 615a. Depending on the application and the battery type, the battery 620 can be housed in the upper 615a or lower 615b control unit, as appropriate.

Of course, the definition of safe and unsafe can vary depending upon the application. If conducting MRIs is the primary concern, for example, then electronics containing ferrous metals can be classified as unsafe, while non-ferrous components can be considered safe. If the primary concern is optical imaging, on the other hand, then electronics that are relatively optically opaque to the electromagnetic energy source (i.e., absorb or reflect a substantial portion of the radiation) can be classified as unsafe, while electronics that are relatively transparent can be classified as safe. So, for example, for an X-ray, or CT scan, for example, materials that readily affect X-ray imaging can be classified as unsafe, while materials that are relatively invisible to X-rays can be classified as safe. Regardless of definition, in this configuration, unsafe components and/or the battery 620 can be removed prior to testing without disturbing the remainder of the system.

Figure 6C:
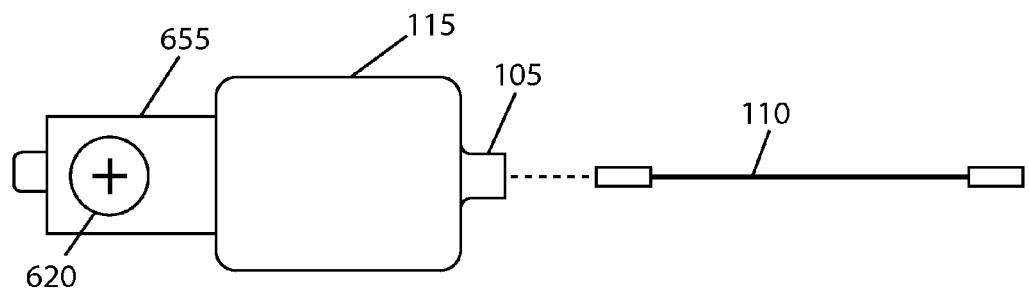
FIG. 6c depicts a modular sensor with a sliding battery bay, in accordance with some examples of the present invention.
Figure 6D:
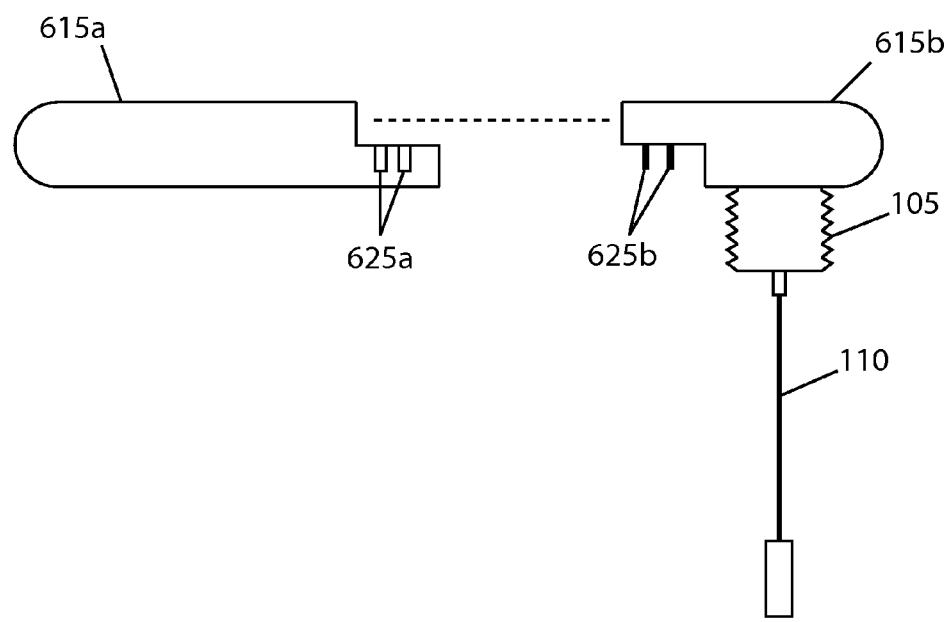
FIG. 6d depicts a modular sensor with an interlocking control unit, in accordance with some examples of the present invention.

In still other examples, as shown in FIG. 6c, the control unit 115 can have a battery compartment 655 to house the battery 620. In this configuration, where all electronic components other than the battery 620 are considered safe, for example, or electronics are simply not a concern, the battery 620 can be easily and quickly removed and/or replaced. One of skill in the art will recognize that the battery compartment 655 can be sliding, as shown, or can be many other configurations (e.g., a simple cover with a battery bay) that enable the battery 620 to be conveniently removed. Removing the battery 620 can obviate the need for expensive, application-specific (e.g., MRI safe) batteries, for example.

The battery 620 can provide power to the system 100 to enable, for example and not limitation, data logging, transmission, and processing. In this manner, the system 100 can store data independently for a predetermined amount of time to be batch downloaded or uploaded. In this manner, network bandwidth usage, for example, can be reduced. In some examples, the control unit 115 can further include one or more processors to enable onboard processing of data from the sensor 110 prior to downloading.

In some examples, as shown in 6d, the upper 615a and lower 615b control units can be coupled using a tongue and grooved type snap fastener, or other suitable means, to provide a lower profile. As above, the control units 615a, 615b can have complementary contacts 625 to provide electrical connections therebetween. One of skill in the art will recognize that the control units 615a, 615b can be physically and electrically connected using many suitable configurations. In some examples, the upper 615a and lower 615b control units can snap together with appropriate plugs or, for example and not limitation can be magnetically retained.

Figure 7A:
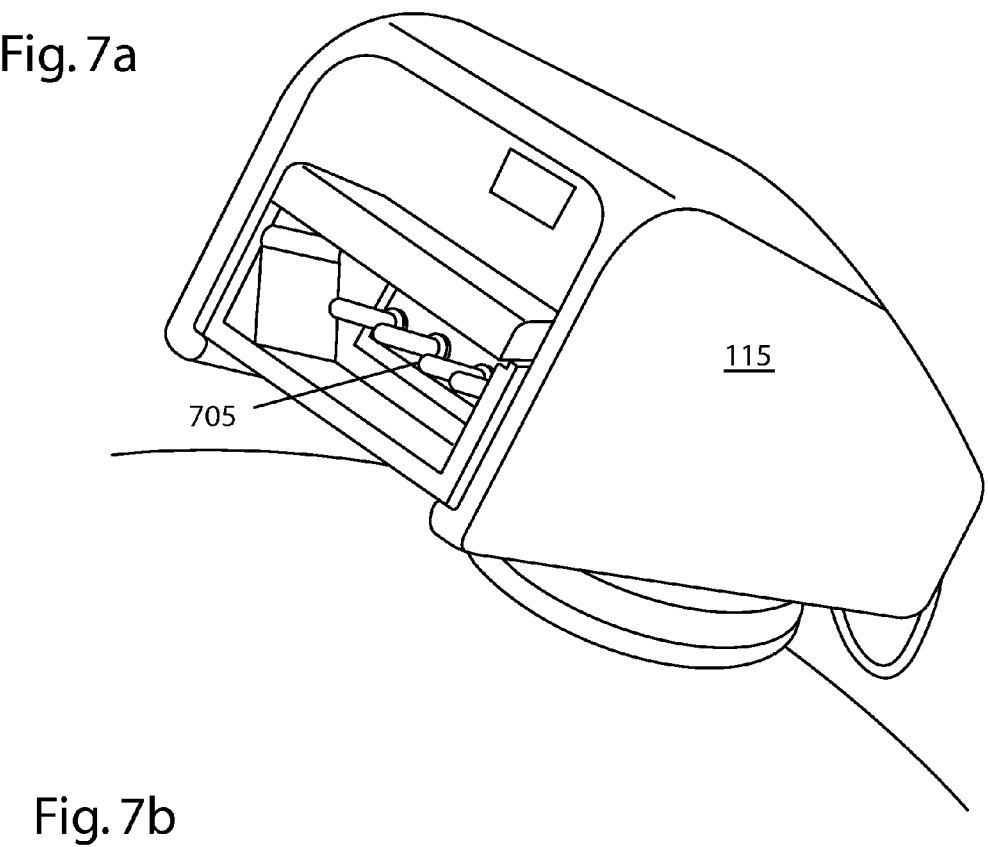
FIG. 7a depicts a first wired interface for the system, in accordance with some examples of the present invention.
Figure 7B:
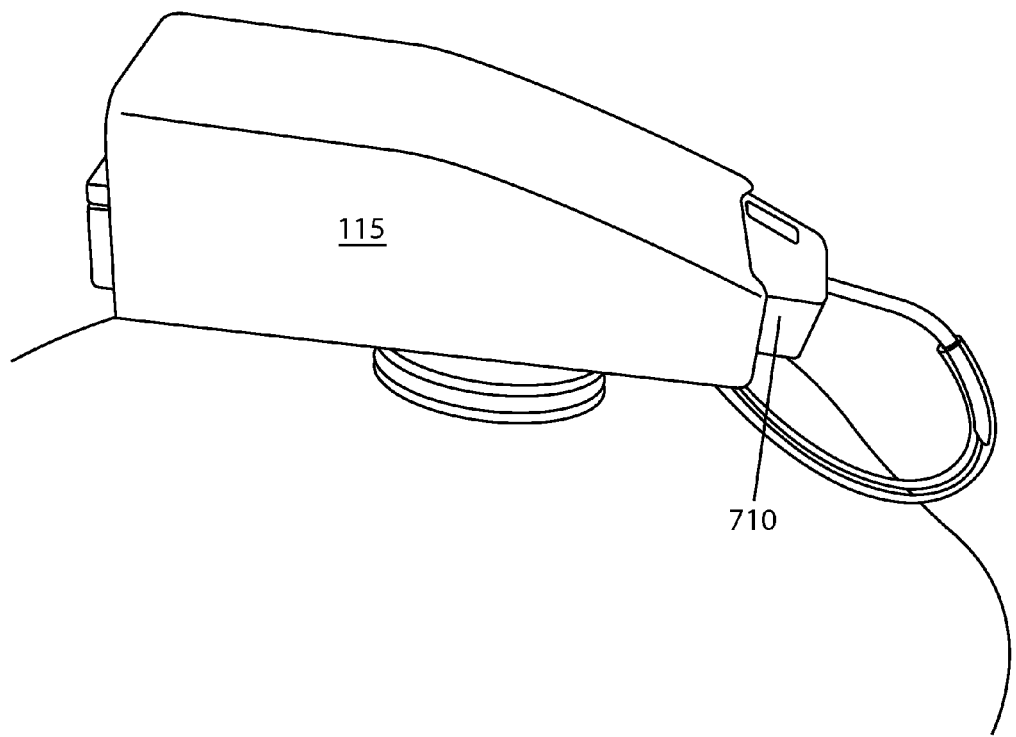
FIG. 7b depicts a second wired interface for the system, in accordance with some examples of the present invention.

As shown in FIGS. 7a-7b, in some examples, the control unit 115 can further include one or more plugs or interfaces 705, 710. The interfaces 705, 710 can be used, for example and not limitation, to charge the batteries, upload and update software, and upload and download data. In some examples, the interfaces 705, 710 can be utilized, for example, to upload software and/or firmware updates to the control unit 115 electronics. The interfaces 705, 710 can also be used to download data from the control unit 115 (e.g., in the event of battery failure), to wipe data from the unit 115, or when a wireless connection is unavailable due to, for example and not limitation, interference or lack of bandwidth. In some examples, the interfaces 705, 710 can also be used to charge the batteries using a suitable cord and power supply (e.g., similar to a cell phone).

As discussed above, a problem with convention sensors, whether they are wired, semi-wired, or wireless has been that the electronic portions of the sensors cannot be easily removed. In many cases, for example, the sensor, sometimes including a catheter, electronics, batteries, and other components are integral (i.e., one inseparable piece). As a result, when the need arises for the patient to have certain procedures such as, for example, an MRI, the entire sensor must be removed from the patient's body. If continued brain monitoring is needed, therefore, a new sensor must be reinstalled and the probe reinserted into the ICC. Each removal and reinstallation, however, represents a risk for injury, infection, and pain for the patient, among other things.

In addition, certain materials, such as ferrous metals, cannot be placed in an MRI machine. The intense magnetic field created by modern MRI machines can actually pull metal objects, including surgically implanted sensors out of the patient's body. This not only can result in obvious injury to the patient, but excruciating pain during the procedure. Even magnetic inks found in some older tattoos have been known to cause burns and moderate to severe discomfort.

To address this issue, as discussed, some or all of the electronics for the system 100 can be stored in the detachably coupleable control unit 115. The control unit 115 can be detachably coupled to the electronics interface 410 or the mounting unit 105 and can be removed without disturbing the mounting unit 105 and/or sensors 110. When necessary or desirable, therefore, the control unit 115 can be removed to enable testing (e.g., MRI, X-ray, etc.) and then reinstalled afterward. In this manner, pain and danger to the patient are minimized and interference with imaging and other procedures is minimized or eliminated.

While several possible examples are disclosed above, examples of the present invention are not so limited. For instance, while several possible sensors have been disclosed, other sensors or combinations of sensors could be selected without departing from the spirit of examples of the invention. In addition, the location and configuration used for the control unit, mounting unit, electronics interface, and other components can be varied based on patient physiology, the type of sensor used, and/or the mounting location on the patient. Modifications can be made to account for, for example, the materials used and/or space or power constraints. Such changes are intended to be embraced within the scope of the invention.

The specific configurations, choice of materials, and the size and shape of various elements can be varied according to particular design specifications or constraints requiring a device, system, or method constructed according to the principles of the invention. Such changes are intended to be embraced within the scope of the invention. The presently disclosed examples, therefore, are considered in all respects to be illustrative and not restrictive. The scope of the invention is indicated by the appended claims, rather than the foregoing description, and all changes that come within the meaning and range of equivalents thereof are intended to be embraced therein.

What is claimed is:

1. A sensor system comprising:
a sensor for monitoring one or more bodily functions of a patient's body;
a lower control unit comprising a first group of one or more electronic components in communication with the sensor;
an upper control unit comprising a second group of one or more electronic components in communication with the sensor; and
a mounting unit detachably coupling the upper and lower control unit to the patient's body;
wherein the upper control unit and the lower control unit can be separately removed from the mounting unit;
wherein removing the upper control unit and the lower control unit from the mounting unit removes all electronic components from the patient's body, while the sensor and mounting unit remain in contact with the patient;
wherein the first group of one or more electronic components comprises safe electronic components, comprising one of non-ferrous containing electronic components and electronics that cause substantially no imaging artifacts during electromagnetic imaging; and
wherein the second group of one or more electronic components comprises unsafe electronic components, comprising one of ferrous containing electronic components and electronics that cause one or more imaging artifacts during electromagnetic imaging.

2. The sensor system of claim 1, further comprising an electronics interface detachably coupled to the mounting unit;
wherein the upper and lower control units detachably couple to the electronics interface.

3. The sensor system of claim 1, further comprising an electronics interface integral to the mounting unit;
wherein the upper and lower control units detachably couple to the electronics interface.

4. The sensor system of claim 1, wherein the upper control unit further comprises a battery.

5. The sensor system of claim 4, wherein the battery is detachably coupled to the upper control unit such that the battery is removable from the sensor system without removing the upper control unit.

* * * * *